US008932629B2

(12) United States Patent
Li et al.

(10) Patent No.: US 8,932,629 B2
(45) Date of Patent: Jan. 13, 2015

(54) CO-PROCESSED MICROCRYSTALLINE CELLULOSE AND SUGAR ALCOHOL AS AN EXCIPIENT FOR TABLET FORMULATIONS

(75) Inventors: Jian-Xin Li, North Brunswick, NJ (US); Brian Carlin, Lawrenceville, NJ (US); Thomas Ruszkay, Hockessin, DE (US)

(73) Assignee: FMC Corporation, Philadelphia, PA (US)

( * ) Notice: Subject to any disclaimer, the term of this patent is extended or adjusted under 35 U.S.C. 154(b) by 805 days.

(21) Appl. No.: 11/925,235

(22) Filed: Oct. 26, 2007

(65) Prior Publication Data

US 2008/0131505 A1  Jun. 5, 2008

Related U.S. Application Data

(60) Provisional application No. 60/855,106, filed on Oct. 27, 2006, provisional application No. 60/928,166, filed on May 8, 2007, provisional application No. 60/855,066, filed on Oct. 27, 2006.

(51) Int. Cl.
*A61K 9/20* (2006.01)
*B27N 3/00* (2006.01)
*A61K 9/16* (2006.01)

(52) U.S. Cl.
CPC ............ *A61K 9/1623* (2013.01); *A61K 9/1652* (2013.01); *A61K 9/1682* (2013.01); *A61K 9/2018* (2013.01); *A61K 9/2054* (2013.01)
USPC .......................................... 424/464; 264/109

(58) Field of Classification Search
CPC .. A61K 9/1623; A61K 9/1652; A61K 9/2018
See application file for complete search history.

(56) References Cited

U.S. PATENT DOCUMENTS

| | | |
|---|---|---|
| 2,978,446 A | 4/1961 | Battista et al. |
| 3,145,146 A | 8/1964 | Lieberman et al. |
| 3,146,168 A | 8/1964 | Battista |
| 3,539,365 A | 11/1970 | Durand et al. |
| 3,639,169 A | 2/1972 | Broeg et al. |
| 4,693,750 A | 9/1987 | Bauer et al. |
| 4,744,987 A | 5/1988 | Mehra et al. |
| 4,980,193 A | 12/1990 | Tuason, Jr. et al. |
| 5,366,742 A | 11/1994 | Tuason, Jr. et al. |
| 5,415,804 A | 5/1995 | Minami et al. |
| 5,573,777 A | 11/1996 | Serpelloni et al. |
| 5,605,712 A | 2/1997 | Bertrand et al. |
| 5,709,896 A | 1/1998 | Hartigan et al. |
| 5,725,886 A | 3/1998 | Erkoboni et al. |
| 5,747,067 A | 5/1998 | Augello et al. |
| 5,789,004 A | 8/1998 | Hogan et al. |
| 5,866,166 A | 2/1999 | Staniforth et al. |
| 6,106,865 A | 8/2000 | Staniforth et al. |
| 6,235,947 B1 | 5/2001 | Yoshinari et al. |
| 6,264,981 B1 | 7/2001 | Zhang et al. |
| 6,432,448 B1 | 8/2002 | Augello et al. |
| 6,440,474 B1 | 8/2002 | Buliga et al. |
| 6,503,918 B2 | 1/2003 | Yoshinari et al. |
| 6,752,939 B2 | 6/2004 | Gereg |
| 6,753,017 B2 | 6/2004 | Berkulin et al. |
| 6,936,277 B2 | 8/2005 | Staniforth et al. |
| 6,936,628 B2 | 8/2005 | Lee |
| 2004/0121006 A1 | 6/2004 | Narita et al. |
| 2005/0220824 A1 | 10/2005 | Kessel et al. |
| 2005/0266116 A1 | 12/2005 | Teckoe et al. |
| 2006/0127451 A1 | 6/2006 | Augello et al. |
| 2008/0131543 A1 | 6/2008 | Teckoe |

FOREIGN PATENT DOCUMENTS

| | | | |
|---|---|---|---|
| EP | 1-226-818 A | 7/2002 | |
| EP | 1-681-048 A | 7/2006 | |
| JP | 11-199517 | 7/1999 | |
| WO | WO 81/02521 A1 | 9/1981 | |
| WO | WO-00/04862 A | 2/2000 | |
| WO | WO 01/19348 A1 | 3/2001 | |
| WO | WO 03103629 | * 12/2003 | ............... A61K 9/00 |
| WO | WO-2005/030177 A | 4/2005 | |
| WO | WO 2005030177 | * 4/2005 | ............... A61K 9/20 |
| WO | WO 2006/034397 | 3/2006 | |

OTHER PUBLICATIONS

Hsiu-O Ho et al., Characteristics of codried products of microcrystalline cellulose with sacharides and low-substituted hydroxypropylcellulose, *Powder Technology*, 127(2002) 45-53.

M. C. Gohel, A review of co-processed directly compressible excipients, *J. Pharm. Pharmaceut. Sci.*, 8(1): 76-93, 2005.

Schroder Rudolf, Hausler, Olaf, Schwartz, Eugen, Seffens, Klaus-Jurgen, "Influence of Magnesium Stearate on the Compaction Behavior and Tablet Characteristics of Co-Spray dried Compounds vs Physical Blends"—Poster presented at American Association Pharmaceutical Science (Denver) Oct. 2001.

Notification of Transmittal of the International Search Report and The Written Opinion of the International Searching Authority, or the Declaration—Dated May 6, 2008—International Application No. PCT/US2007/022685.

S. Jacob, A. A. Shirwaikir, A. Joseph, K.K. Srinivasan, "Novel Co-Processed Excipients of Mannitol and Microcrystalline Cellulose for Preparing Fast Dissolving Tablets of Glipizide" Indian Journal of Pharmaceutical Sciences, vol. 69 (5) Sep.-Oct. 2007 pp. 633 to 639.

Weller P. J. et al. "Cellulose Microcrystalline XP 002-481910 Handbook of Pharmaceutical Excipients". Fourth Edition, 2003, Pharmaceutical Press, London, pp. 108-111.

(Continued)

*Primary Examiner* — Suzanne Ziska
*Assistant Examiner* — Thurman Wheeler
(74) *Attorney, Agent, or Firm* — FMC Corporation

(57) ABSTRACT

A particulate co-processed composition comprising microcrystalline cellulose and at least one sugar alcohol is disclosed. A preferred sugar alcohol is mannitol. The composition has an improved compactability profile, lubricant sensitivity, and ejection profile compared to microcrystalline cellulose and the at least one sugar alcohol, either alone or in combination as a simple dry blend, in the preparation of solid dosage formulations, such as tablets. Tablets comprising the particulate co-processed composition, an active, and, optionally, one or more other excipients, and method for their preparation, are also disclosed.

13 Claims, 7 Drawing Sheets

(56) References Cited

OTHER PUBLICATIONS

Mitchell S. A. et al. "A Compaction Process to Enhance Dissolution of Poorly Water-Soluble Drugs Using Hydroxypropyl Methylcellulose". International Journal of Pharmaceutics, 250, 3-11, 2003.

Kleinebudde, P. "Roll Compaction/Dry Granulation: Pharmaceutical Applications". European Journal of Pharmaceutics and Biopharmaceutics, 58, 317-326, 2004.

DeYampert Rogers, Tracey L., "Content Considerations for Low Dosage Drug Formulations Processed by Roller Compaction". Ph.D. Thesis, Purdue University, Aug. 1997.

Falzone, Angela Marie, "Roller Compaction of Pharmaceutical Excipients and Excipient-Drug Blends". Ph.D. Thesis, Purdue University, Dec. 1990.

Skinner G.W. "The Evaluation of Fine-particle Hydroxypropylcellulose as a Roller Compaction binder in Pharmaceutical Applications". Drug Development & Indus. Pharm, 25(10), 1121-1128 (1999).

The Fitzpatrick Company Europe N.V., "Introduction to Roll Compaction and the Fitzpatrick Chilsonator", Mar. 1997.

Sheskey P. et al. "Roll Compaction Granulation of a Controlled-Release Matrix Tablet Formulation Containing HPMC". Pharmaceutical Technology, Oct. 1999.

Zhang Y. et al. "Physical Properties and Compact Analysis of Commonly Used Direct Compression Binders". AAPS Pharm. Sci. Tech. 4(4), Article 62, Dec. 15, 2003.

DeYampert Rogers, Tracey L., "Oral Preliminary Examination", Sep. 1, 1995.

S. Jacob, "Novel Co-Processed Excipients of Mannitol and Microcrystalline Cellulose for Preparing Fast Dissolving Tablets of Glipizide"; Indian Journal of Pharmaceutical Sciences, vol. 69, No. 5, Sep.-Oct. 2007, pp. 633-639.

\* cited by examiner

CO-PROCESSED MICROCRYSTALLINE CELLULOSE AND SUGAR ALCOHOL AS AN EXCIPIENT FOR TABLET FORMULATIONS

CROSS-REFERENCE TO RELATED APPLICATIONS

This application claims priority on U.S. Provisional Application Ser. No. 60/855,106, filed Oct. 27, 2006, on U.S. Provisional Application Ser. No. 60/928,166, filed May 8, 2007, and on U.S. Provisional Application Ser. No. 60/855,066, filed Oct. 27, 2006, the disclosures of which are all incorporated herein by reference.

FIELD OF THE INVENTION

The present invention relates to a composition for use in the manufacture of pharmaceuticals, and in particular, solid dosage forms such as tablets. In particular, this invention relates to co-processed microcrystalline cellulose (MCC) with a sugar alcohol, such as mannitol, and its use in tablet formulations.

BACKGROUND OF THE INVENTION

Discrete dosages of pharmaceutical compositions suitable for oral administration are conveniently administered as solid dosage forms, typically tablets. In addition to the therapeutic ingredient or ingredients (commonly referred to as "actives," "active pharmaceutical ingredients," or "API"), the tablet comprises pharmaceutically acceptable materials, known as excipients, that are not actives and do not provide a therapeutic effect, but are added to the tablet formulation to confer specific properties not related to the activity of the active.

There are three general methods of preparation of tablets: (1) direct compression or tabletting; (2) dry granulation; and (3) wet granulation. In direct compression, the powdered material(s) to be included in the tablet (including the active and the excipients) are blended together and compressed directly without intermediate processing such as granulation. Dry granulation procedures may be used where poor flow or low bulk density of the direct compression mix precludes direct compression. The method includes mixing the ingredients, roller compacting or slugging the mix, dry screening or milling the coarse dry granuloate, lubricating and finally compressing the lubricated granules. The wet granulation procedure includes mixing some or all of the ingredients of the dosage form and thereafter adding solutions of a binding agent to the mixed powders to obtain a granulation. Thereafter, the damp mass is screened, and dried, e.g., via tray drying, the use of a fluid-bed dryer, spray-dryer, radio-frequency dryer, microwave, vacuum, or infra-red dryer.

Because direct compression requires fewer unit operations than wet granulation, it is a less expensive process. This means less equipment, lower power consumption, less space, less time, and less labor leading to reduced production cost of tablets. However, direct compression is limited to those situations where the compression mix has the requisite physical characteristics required for formation of a pharmaceutically acceptable tablet. Because the tablet formulation is compressed to prepare the tablet, the formulation must possess physical characteristics that lend themselves to processing in such a manner. Among other things, the tablet formulation must be free-flowing, must be lubricated, and, importantly, must possess sufficient binding to insure that the tablet remains intact after compression.

Tablets are formed by the application of pressure to the tablet formulation on a tablet press. A tablet press includes a lower punch which fits into a die from the bottom and an upper punch having a corresponding shape and dimension, which enters the die cavity from the top after the tablet formulation fills the die cavity. The tablet is formed by pressure applied on the lower and upper punches. The ability of the tablet formulation to flow freely into the die is important in order to insure that there is a uniform filling of the die and a continuous movement of the tablet formulation from its source. The tablet must also eject cleanly from the die following compression. Typically, a lubricant is added to the tablet formulation to avoid sticking to the die and to cause the formulation to flow freely.

Because of its inherent compactability characteristics, microcrystalline cellulose (MCC) is widely used as an excipient in tablet formulations. Good binding and disintegration properties are obtained with microcrystalline cellulose when used it is used in direct compression tablet formulations. However, microcrystalline cellulose can have lubricant sensitivity. Lubricant sensitivity refers to the reduction in bonding between the plastically-deforming particles in the powder due to the addition of lubricant, which leads to reduction in tablet strength or hardness. Lubricant sensitivity is the ratio of the unlubricated compactability of the tablet formulation to the lubricated compactability of the tablet formulation.

Tablet manufacturing has changed by the introduction of the direct compression process and high-speed machines. These two developments have increased the demands on the functionality of excipient in terms of flow and compression properties. Thus, a need exists for an excipient with superior functionalities particularly high compactability, low lubricant sensitivity, and low ejection force profile that makes it an ideal candidate for tablet formulations, particularly for direct compression.

SUMMARY OF THE INVENTION

The inventors have surprisingly found that MCC co-processed with a sugar alcohol has better compactability and other desirable functional properties for the preparation of solid dosage forms, such as tablets, than MCC or a sugar alcohol when used alone or in combination in a physical mixture, such as in a dry blend.

In one aspect, the invention is a co-processed composition of microcrystalline cellulose (MCC) and at least one sugar alcohol, in which the ratio of microcrystalline cellulose to the at least one sugar alcohol is 99:1 to 1:99. The at least one sugar alcohol typically has at least four carbon atoms. The ratio of the compactability of an unlubricated composition to the compactability of a lubricated composition is 1.9 or less, or 1.8 or less, or 1.6 or less, when the lubricated composition additionally comprises about 1% magnesium stearate. A preferred sugar alcohol is mannitol.

The co-processed composition has superior functionalities. It has higher compactability, reduced lubricant sensitivity, and lower ejection force profile, relative to the individual ingredients of the co-processed composition, either singly or as a dry blend. The co-processed composition has reduced reactivity towards actives. These properties make the co-processed composition an ideal excipient for solid dosage formulations, such as tablets, that include one or more actives. The co-processed composition is particularly useful as binder for tablet formulations processed by direct compression.

In yet another aspect, the invention is a method of preparation of the co-processed composition, the method comprising the steps of: (a) forming an aqueous slurry of microcrystalline cellulose, a sugar alcohol, and, optionally, a pH modifier, the slurry having a solids content and temperature to ensure dissolution of sugar alcohol, and (c) drying the slurry. A preferred pH modifier is ammonium hydroxide, and a preferred drying method is spray drying.

In another aspect, the invention is a compressible tablet formulation comprising one or more actives, the co-processed composition of the invention, optionally, one or more excipients, and, optionally, one or more lubricants. In another aspect, the invention is a method for forming a solid dosage formulation by compressing the tablet formulation. In still another aspect, the invention is tablet or a solid dosage formulation made by compressing the tablet formulation.

DETAILED DESCRIPTION OF THE INVENTION

Figure 1A:
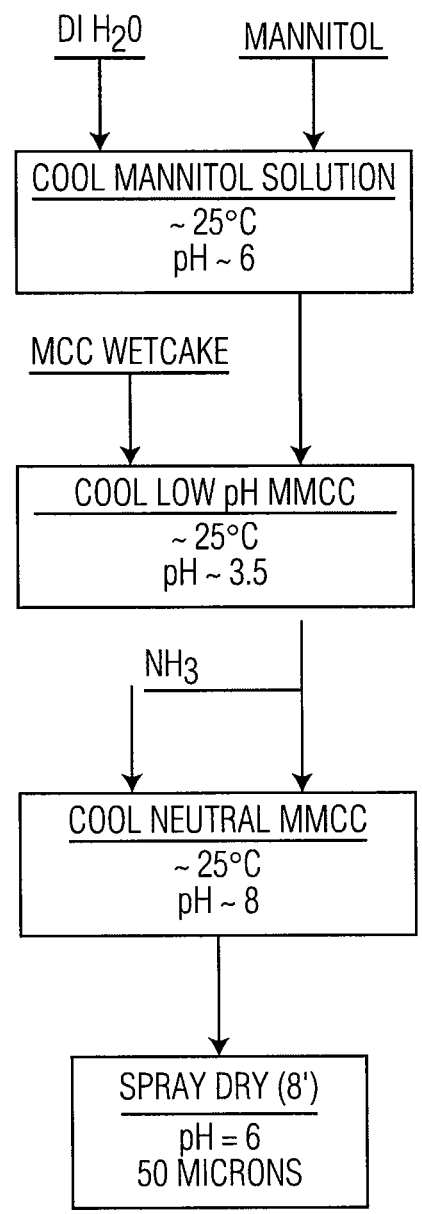
FIGS. 1A and 1B show processes used to prepare co-processed MCC/mannitol.

Unless the context indicates otherwise, in the specification and claims, the terms active, excipient, lubricant, sugar alcohol, cellulose derivative, pH modifier, and similar terms also include mixtures of such materials. Unless otherwise specified, all percentages are percentages by weight and all temperatures are in degrees Centigrade (degrees Celsius).

Microcrystalline Cellulose

Microcrystalline cellulose (MCC) is purified, partially depolymerized cellulose, which may be obtained by hydrolysis of various cellulose sources, such as wood, wood pulps such as bleached sulfate and sulfate pulps, cotton, flax, hemp, bast or leaf fibers, regenerated forms of cellulose, soy hulls, corn hulls, or nut hulls. It is a white, odorless, tasteless, relatively free flowing powder that is insoluble in water, organic solvents, dilute alkalis and dilute acids.

Hydrolysis may be accomplished by any of several well-known methods. Generally, the source of cellulose, preferably a source of alpha-cellulose, in the form of a pulp from fibrous plants, is treated with a mineral acid, preferably hydrochloric acid. The acid selectively attacks the less ordered regions of the cellulose polymer chain, thereby leaving the more crystalline regions, which constitute microcrystalline cellulose. The MCC is then separated from the reaction mixture and washed to remove by-products. The resulting wet mass, generally containing 40-60 wt % moisture, is referred to by several names, including hydrolyzed cellulose, microcrystalline cellulose, microcrystalline cellulose wetcake, or simply wetcake. Preparation of microcrystalline cellulose is disclosed in Battista, U.S. Pat. Nos. 2,978,446 and 3,146,168, the disclosures of which are incorporated herein by reference.

Microcrystalline cellulose is commercially available under the trade name EMCOCEL® from Edward Mendell Co., Inc. and as AVICEL® from FMC Corp. Several grades of microcrystalline cellulose that vary in particle size, density and moisture content are available, for example, AVICEL® PH-101, PH-102, PH-103, PH-105, PH-112, PH-113, PH-200, PH-301, and PH-302.

Sugar Alcohols

Sugar alcohol refers to polyhydroxy alcohols that include acyclic or alicyclic polyols. Acyclic sugar alcohols have the general formula $C_nH_{n+2}(OH)_n$. Typical sugar alcohols include, for example, mannitol, sorbitol, xylitol, lactitol, isomalt, maltitol, erythritol, and threitol. Preferred sugar alcohols are those containing four to six carbon atoms (i.e, n is 4 to 6), especially five or six carbon atoms (n is 5 or 6).

A particularly preferred sugar alcohol is mannitol [($C_6H_8(OH)_6$)] [(2R,3R,4R,5R)-hexane-1,2,3,4,5,6-hexol] [CAS #69-65-8]. Mannitol is non-hydroscopic, produces solutions with relatively low viscosity, and has a relatively high melting point (about 167-170° C.). These properties allow aqueous microcrystalline cellulose/mannitol slurries to be readily spray dried to produce co-processed microcrystalline cellulose/mannitol.

Co-Processed Composition

The co-processed composition comprises two components, microcrystalline cellulose and at least one sugar alcohol. The two components are present at a weight ratio of about 99:1 to 1:99 microcrystalline cellulose:sugar alcohol, typically about 70:30 to 95:5, more typically about 75:25 to 95:5, for example, 90:10. Minor amounts of water may also be present. The moisture content is about 0.5% to about 15% by weight, preferably about 2.5% to about 6% by weight, and most preferably about 3.0% to about 5% by weight.

The co-processed composition is a particulate composition that has an average mean particle size of about 20 microns to about 1000 microns. The mean particle size is typically about 50 microns to about 200 microns, more typically about 70 microns to about 120 microns, and even more typically 80 microns to 110 microns, for example, about 90 microns. The loose bulk density (LBD) of the co-processed composition is typically less than or equal to 0.60 g/cm$^3$. The loose bulk density of the co-processed composition, with a component ratio of 70:30 to 95:5 microcrystalline cellulose:mannitol, for example, is typically about 0.35-0.45 g/cm$^3$. The pH is about 3.0 to about 8.5, preferably about neutral.

The co-processed composition possesses desirable performance attributes that are not shown with the corresponding dry blend of microcrystalline cellulose and the sugar alcohol. The reason is not fully understood. Although not being bound by any theory or explanation, it appears that co-processing yields a composition in which the two essential components are in intimate association with each other. This intimate association or admixture of microcrystalline cellulose and the sugar alcohol cannot be achieved through simple dry blending of these materials, but rather requires that they be co-processed as an aqueous slurry or mixture, prior to drying of the slurry.

The compactability of the co-processed composition compares favorably with that of commercially available microcrystalline celluloses. Compactability is defined as the slope of the plot of tablet hardness (sometimes referred to as tensile strength) vs. compression force. The compactability of an excipient is desirably high, because lower levels of excipient may then be used in tabletting, with concurrent larger amounts of active being present, without compromising tablet performance characteristics.

The hardness or tensile strength generally required for tablets is about 2 MPa. Although hardness values measured for the co-processed compositions are typically greater than this value, these values were measured on compact tablets containing only the unformulated composition. It is anticipated that the hardness values for formulated tablets, which comprise other ingredients, will be somewhat lower.

The co-processed microcrystalline cellulose/sugar alcohol composition has lower lubricant sensitivity, and its compaction profile is relatively less affected when used with lubricants. In contrast, the compression profile for microcrystalline cellulose by itself shows greater lubricant sensitivity, with higher compression forces being required to produce the same tablet hardness as for the equivalent lubricant-free tablets. In many cases, simply increasing the compression force would not compensate for reduced compactability due to lubricant addition. The flow characteristics of the co-processed composition are good, and thus ideal for high speed direct compression tabletting equipment.

Lubricant sensitivity is defined as the ratio of the unlubricated compactability of a composition to the lubricated compactability of the composition. The co-processed microcrystalline cellulose/sugar alcohol compositions typically have a lubricant sensitivity of 1.9 or less, typically 1.8 or less, when the lubricated composition comprises about 1% magnesium stearate lubricant.

Co-Processing

The process for preparing the co-processed composition involves forming a well-dispersed aqueous slurry of microcrystalline cellulose and a sugar alcohol, for example mannitol. The slurry may be formed by using microcrystalline cellulose wetcake formed in the hydrolysis step during the manufacture of microcrystalline cellulose, or in may be formed by re-slurrying dried microcrystalline cellulose. The relative amounts of the two components are adjusted in the slurry to yield the specific weight ratio desired in the final dried co-processed composition. In some instances, it may be desirable to form the slurry under conditions of low shear.

Then the aqueous slurry is dried by removing water from it to yield the co-processed composition. Preferably, the slurry is dried using spray-drying techniques, which are well known in the art. Other drying techniques, however, such as flash drying, ring drying, tray drying, vacuum drying, radio frequency drying, and microwave drying, can also be used.

The microcrystalline cellulose is preferably wetcake from a conventional microcrystalline cellulose manufacturing process. Wetcake is microcrystalline cellulose that has not yet been dried to yield conventional microcrystalline cellulose as a free-flowing powder. The particle size of the microcrystalline cellulose used in the aqueous slurry is ordinarily that which is encountered in conventional microcrystalline cellulose manufacture. pH adjustment of the wetcake can be made before, during, or after the sugar alcohol addition, preferably before, as representative of conventional MCC manufacturing processes.

The aqueous slurry of these two components may be prepared in any of several ways. The sugar alcohol may be introduced into the microcrystalline cellulose slurry as solid or pre-dissolved in water. Typically the solids concentration is about 5-25 wt % microcrystalline cellulose, preferably about 10-20 wt % microcrystalline cellulose. The exact amount of sugar alcohol to be added depends on the microcrystalline cellulose content of the slurry and the ratio of the two components desired in the co-processed composition. Water may also be added if a more dilute slurry is required The total solids content of the aqueous slurry is preferably at least 10 wt %, based on the total slurry weight, and is more preferably at least 20 wt % solids. The higher solids content levels are desirable since the amount of water that must be removed during the drying step is accordingly reduced. The upper limit on solids content in the aqueous slurry is typically determined by the operating constraints of the drying apparatus used. With the preferred spray drying procedure, solids contents of 20-30 wt % are representative for aqueous slurries that can be readily processed. Ambient or elevated slurry temperatures, of from about 10° C.-80° C. may be used, and higher slurry temperatures may be desirable with certain types of drying equipment.

The drying of the well-dispersed aqueous slurry is preferably accomplished by spray drying. Conventional spray drying equipment may be used. Operating procedures familiar to those skilled in the spray drying art are applicable to the spray drying step of this process. Drier outlet temperature is ordinarily used to control the residual moisture level obtained in the co-processed composition.

Depending upon the amount and type of drying, the concentration of the microcrystalline cellulose and sugar alcohol in the slurry the co-processed composition will have different particle sizes, densities, pH and moisture content. It is for this reason that the drying step in the co-processing procedure is especially critical, and it is the reason that spray drying is the preferred method for accomplishing the drying step.

Spray drying the well-dispersed aqueous slurry produces a co-processed composition having a loose bulk density of less than or equal to 0.60 g/cm$^3$, suitably 0.20 g/cm$^3$ to 0.60 g/cm$^3$. This produces a composition having a preferred compactability in the presence of lubricant compared to either a dry blend of the materials or the corresponding wet granulate. The loose bulk density may be less than 0.55 g/cm$^3$, less than 0.50 g/cm$^3$, less than 0.45 g/cm$^3$, less than 0.40 g/cm$^3$, less than 0.35 g/cm$^3$, less than 0.30 g/cm$^3$, and less than 0.25 g/cm$^3$.

The co-processed composition recovered from the drying operation is a free-flowing particulate solid. Particle size of the product is a function of the spray drier settings, which can be controlled by those skilled in the art such as adjusting feed rates and atomizer disc speeds during spray drying.

Solid Dosage Formulations

The solid dosage form comprises the co-processed composition of the invention, one or more actives, optionally, one or more one or more pharmaceutically acceptable excipients, and, optionally, one or more pharmaceutically acceptable lubricants. Typical tablet formulations are prepared by combining the active or actives with at least one excipient, if present, and the at least one lubricants, if present, according to conventional pharmaceutical compounding techniques. To prepare a solid dosage form, or tablet, by direct compaction, the tablet formulation must have the necessary physical characteristics. Among other things, the tablet formulation must be free flowing, must be lubricated, and, importantly, must possess sufficient compactability to ensure that the solid dosage form remains intact after compaction, and is robust enough for subsequent operations, such as handling, coating, and packaging.

The tablet is formed by pressure being applied to the tablet formulation on a tablet press. A tablet press includes a lower punch that fits into a die from the bottom and an upper punch having a corresponding shape and dimension that enters the die cavity from the top after the tablet formulation fills the die cavity. The tablet is formed by pressure applied on the lower and upper punches. The ability of the tablet formulation to flow freely into the die is important in order to ensure that there is a uniform filling of the die and a continuous movement of the material from the source of the tablet formulation, e.g. a feeder hopper. The lubricity of the tablet formulation is crucial in the preparation of the solid dosage forms since the compressed material must be readily released from the punch faces. The tablet must also eject cleanly from the die following compression.

Because actives do not always have these properties, methods of tablet formulation have been developed in order to impart these desirable characteristics to the tablet formulation. Typically, the tablet formulation comprises one or more additives, or excipients, that impart the desired free flowing, lubrication, and binding properties to the tablet formulation.

The excipients should not accelerate chemical and/or physical degradation of the active and should not interfere with its biological availability. The excipients should be physiologically inert and should not unintentionally interfere with the tablet disintegration or dissolution of the active. They should show low lubricant sensitivity and ensure acceptable active content uniformity. Typical excipients are selected from the group consisting of a disintegrants, glidants, fillers, diluents, colorants, flavorants, stabilizers, and lubricants. The choice of the excipients and the composition of the tablet formulation depend on the active, the amount of active in the formulation, the type of tablet, the desired characteristics for both the tablet formulation and the resulting tablet, and the manufacturing process used. The excipients for dry granulate formulations should have good recompactability and dilution potential to allow compaction of the granules into a tablet. These include prompt release, for which the drug dissolves in a very short time, immediate release and modified release, which include most of the orally administered tablets that are swallowed.

Pharmaceutically acceptable excipients are well known to those skilled in the art and are disclosed for example, in Staniforth, U.S. Pat. No. 6,936,277, and Lee, U.S. Pat. No. 6,936,628, the disclosures of which are incorporated herein by reference. MCC is added to improve the compactability of the tablets. Excipients such as diluents, binders, glidants, and lubricants are added as processing aids to make the tabletting operation more effective. Still other types of excipients enhance or retard the rate of disintegration of the tablet, improve the taste of the tablet, (for example, sweetening agents), or impart a color or flavor to the tablets.

Lubricants are typically added to prevent the formulation from sticking to the punches during tablet manufacture. Commonly used lubricants include magnesium stearate and calcium stearate. Lubricants typically comprise about 0.5 wt % to about 3.0 wt % of the formulation. Antiadherents prevent sticking of the tablet formulation to the punch face and die wall. They are used in combination with magnesium stearate when sticking is a problem. Commonly used antiadherents are cornstarch and talc.

Diluents, fillers, or bulking agents are frequently added in order to increase the bulk weight of the material to be tabletted in order to make the tablet a practical size. This is often necessary where the dose of the active is relatively small. Typical fillers include lactose, dicalcium phosphate, calcium carbonate, powdered cellulose, dextrates, mannitol, starch, pre-gelatinized starch, and mixtures thereof. Sugar alcohols, such as, sorbitol, mannitol and xylitol are also used as fillers, especially in chewable tablet formulations. The most significant differences between sorbitol and mannitol are hygroscopicity and solubility. Sorbitol is hygroscopic above 65% relative humidity and mannitol is nonhygroscopic. The aqueous solubility of sorbitol is higher than mannitol.

Binders are added to impart cohesive qualities to the powdered material(s). Commonly used binders include starch, microcrystalline cellulose, and sugars such as sucrose, glucose, dextrose, and lactose. Stabilizers reduce the rate at which the active decomposes. Typical stabilizers are antioxidants such as ascorbic acid. Disintegrants are often added to ensure that the tablet has an acceptable dissolution rate in an environment of use (such as the gastrointestinal tract). The disintegrant breaks up the tablets and the granules into particles of active and excipients. Although MCC and partially pregelatinized starch are frequently used in formulations to perform both the functions of compaction and disintegration it is often necessary to add super-disintegrants such as croscarmellose sodium, sodium starch glycolate, or crospovidone.

Glidants are used in tablet formulations to improve flow. They are more frequently used in dry blend, rather than wet granulated formulations. Because of the shape and size of the particles, glidants improve flow in low concentrations. They are mixed in final tablet formulation in dry form. Most commonly used glidants are alkali metal stearates, colloidal silicon dioxide (CAB-O-SIL®, SYLOID®, AEROSIL®), and talc. Desirable characteristics may be imparted to the tablet by colorants (i.e., dyes and pigments), natural or artificial sweeteners, and flavorants. Wetting agents, also called surface active agents or surfactants, may also be present. The tablet may also be coated.

The size of round tablets is typically about 50 mg to 500 mg and for capsule-shaped tablets about 200 mg to 1200 mg. However, other formulations prepared in accordance with the invention may be suitably shaped for other uses or locations, such as other body cavities, e.g., periodontal pockets, surgical wounds, and vaginally. For certain uses, such as chewable tablets, antacid tablets, vaginal tablets, and implants, the tablet may be larger.

The compositions are also suitable use in the NRobe® process to prepare solid dose forms. Solid dose forms for the NRobe® process are prepared by lightly compacting a tablet formulation or granulate formulation to form a powder compact and enrobing the powder compact with a film. Methods and apparatus for forming the enrobed solid dose forms are disclosed in WO 03/096963, WO 2005/030115, WO 2005/030116, WO 2005/030379, and WO 2006/032828, the disclosures of which are all incorporated herein by reference.

INDUSTRIAL APPLICABILITY

The co-processed compositions of the invention are ideal excipients for solid dosage formulations, such as tablets, that comprise one or more actives. They are particularly useful as binders for formulations prepared by direct compression. Although primarily used in pharmaceutical/veterinary applications, such tablet technologies may be used in other areas, such as agriculture, food, cosmetics, and other industrial applications. Frequently, the stability active or actives in a tablet comprising a co-processed composition of the invention is greater than the stability of the active or actives in a tablet comprising the same wt % of a non-co-processed dry blend of microcrystalline cellulose and the at least one sugar alcohol, the dry blend having the same weight ratio of the microcrystalline cellulose to the at least one sugar alcohol as the co-processed composition.

The advantageous properties of this invention can be observed by reference to the following examples, which illustrate but do not limit the invention.

EXAMPLES

Glossary

AVICEL® PH-102 Microcrystalline cellulose (FMC, Philadelphia, Pa. USA)
Lactose monohydrate NF (Foremost Farms, Sparta, Wis. USA)
Magnesium stearate (Mallinckrodt, St. Louis, Mo. USA)
PEARLITOL® 100 SD Granular mannitol (100 microns) (Roquette Freres, Lestrem, France)
PEARLITOL® 300 DC Granular mannitol (250 microns) (Roquette Freres, Lestrem, France)
PEARLITOL® 400 DC Granular mannitol (360 microns) (Roquette Freres, Lestrem, France)
PEARLITOL® 500 DC Granular mannitol (520 microns) (Roquette Freres, Lestrem, France)
PROSOLV® 90 Silicified microcrystalline cellulose (JRS Pharma, Patterson N.Y. USA)

General Procedures

The examples set forth the preparation of various microcrystalline cellulose/sugar alcohol compositions. Tablets were prepared using each of the compositions and tested for compactability, lubricant sensitivity, and ejection profiles and compared to tablets made from simple dry blends of MCC and mannitol, as well as controls made with 100% MCC, mannitol, and other co-processed excipient products.

In the following examples, the co-processed compositions are compared to the corresponding blends of the same composition in which the blends are prepared by simple dry mixing of the separate powder components. LOD and LBD are loss on drying and loose bulk density, respectively. Loose bulk density as determined by USP 27 <616> method 2 (Scott volumeter ASTM B329-90), is the minimum density (g/cm$^3$) of the poured powder in the absence of consolidation (e.g. vibration). Compactability refers to the slope of the compaction plot of Hardness vs. Compaction force. Compaction force (kN) or compression force (kN) is reported instead of compaction pressure (MPa). However, because all the determinations were carried out in the same tooling, compaction force and compaction pressure are directly proportional for all measurements.

Lubricant sensitivity can be quantified by the ratio of the unlubricated compactability to the lubricated compactability. Friability was measured using a batch of twenty tablets in a VanKel Friabilator. Weight is measured initially and after 5 min periods up to 30 min. The friability is reported as the percentage weight loss. Disintegration time is determined using a QC-21 Disintegration Test system according to USP methods using six tablets in deionized water at 37° C.

Example 1

Figure 1B:
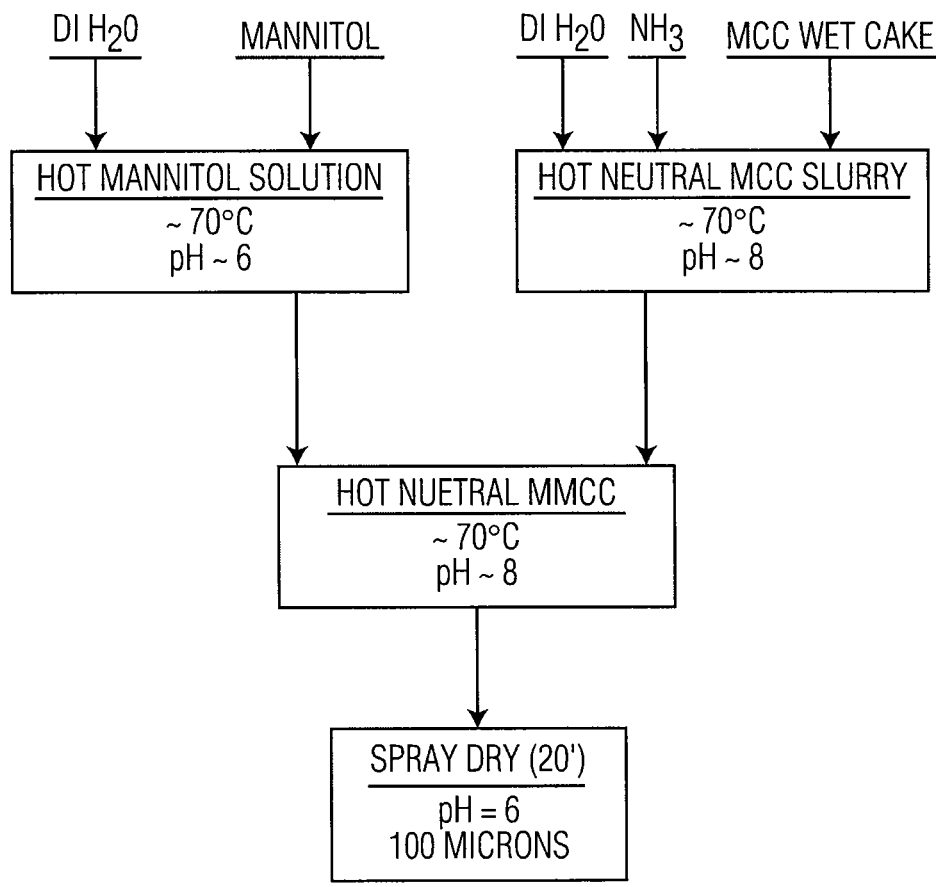

This example illustrates formation of a co-processed microcrystalline cellulose/sugar alcohol by two different processes. FIG. 1A shows Process 1, a cool, low pH process. It uses ambient temperature water and involves adding acid MCC wetcake to a mannitol solution to form a mixture of MCC and mannitol ("MMCC"), which is, optionally, neutralized with ammonia. The resulting slurry ("Cool Neutral MMCC") is spray dried. FIG. 1B shows Process 2, a hot, neutral pH process. Acid MCC wetcake is added to 70° C. water and, if necessary, neutralized with ammonia. Then a 70° C. mannitol solution is added to the neutralized MCC slurry. The resulting slurry ("Hot Neutral MMCC") is spray dried.

Figure 2:
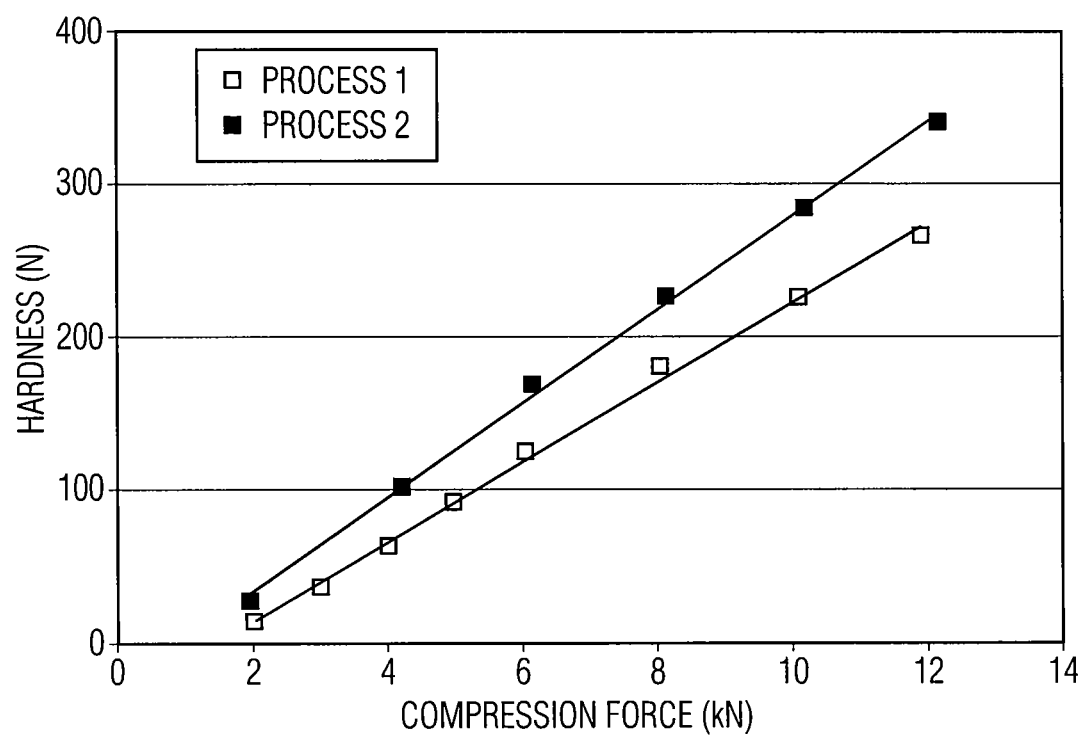
FIG. 2 shows the impact of processing conditions on the compactability of the co-processed MCC/mannitol.

The compaction profiles of 90% MCC/10% mannitol compositions produced by these processes are shown in FIG. 2. There is no significant difference in the compactability of the samples made by processes 1 and 2

Example 2

This example illustrates evaluation of co-processed MCC/sugar alcohol samples prepared by Process 1 of Example 1. MCC (PH grade wetcake) and mannitol (USP/NF grade) were co-processed as described in Process 1 of Example 1. Samples were produced with batch solids content necessary to solubilize all of the mannitol in each batch (mannitol solubility in water, about 18% solids at 25° C., pH about 5.2). Six samples were produced and spray dried on a 2.44 M (8 ft) Bowen dryer using standard MCC operating conditions. Inlet temperature 198-232° C.; outlet temperature 82-118° C. Samples were produced with 25%, 50% and 75% mannitol at two pH levels of 3.7 (unneutralized) and 5.8 (neutralized with NH$_4$OH to pH 8). The physical properties of the samples are summarized in Table 1.

TABLE 1

| Sample # | Mannitol (%) | LOD$^a$ (%) | >200 mesh (75 μm) (%) | LBD$^b$ (g/ml) | pH |
|---|---|---|---|---|---|
| 1-1 | 25 | 2.7 | 7 | 0.39 | 3.7 |
| 1-2 | 50 | 1.7 | 10 | 0.47 | 3.5 |
| 1-3 | 75 | 1.3 | 5 | 0.45 | 3.4 |
| 1-4 | 25 | 1.8 | 8 | 0.41 | 5.7 |
| 1-5 | 50 | 1.4 | 3 | 0.48 | 5.8 |
| 1-6 | 75 | 1.1 | 3 | 0.47 | 6.1 |

$^a$Loss on Drying.
$^b$Loose Bulk Density

Example 3

Five additional samples of co-processed MCC/mannitol were produced as described in Example 2. Samples were produced with 0, 5, 10, 15, & 20% mannitol at pH 6.0. The physical properties of the samples are summarized in Table 2.

TABLE 2

| Sample # | Mannitol (%) | LOD (%) | >200 mesh (75 μm) (%) | LBD (g/ml) | pH |
|---|---|---|---|---|---|
| 2-1 | 0 | 3.0 | 15 | 0.38 | 5.7 |
| 2-2 | 5 | 2.7 | 18 | 0.35 | 6.1 |
| 2-3 | 10 | 2.8 | 21 | 0.37 | 6.1 |
| 2-4 | 15 | 2.3 | 24 | 0.38 | 6.1 |
| 2-5 | 20 | 2.3 | 21 | 0.40 | 6.1 |

Example 4

To identify the lowest level of mannitol required for reduced lubricant sensitivity, three additional samples of co-processed MCC/mannitol were prepared as described in Example 2. Samples were produced with 0.5, 1.0, and 2.5% mannitol at pH 6. The physical properties of the samples are summarized in Table 3.

TABLE 3

| Sample # | Mannitol (%) | LOD (%) | >200 mesh (75 μm) (%) | LBD g/ml | pH |
|---|---|---|---|---|---|
| 3-1 | 0.5 | 3.4 | 21 | 0.40 | 6.1 |
| 3-2 | 1.0 | 3.0 | 25 | 0.38 | 6.1 |
| 3-3 | 2.5 | 3.2 | 31 | 0.37 | 6.1 |

Example 5

This example compares the properties lubricated and unlubricated co-processed MCC/mannitol with those of the corresponding MCC/mannitol blends.

The compactability and lubricant sensitivity of co-processed MCC/mannitol made according to Example 1 were compared with that of the corresponding blends. Unlubricated 1.5 kg blends were prepared by mixing the MCC and mannitol in a V-blender for 4 min. Blends and co-processed compositions were lubricated with 2% magnesium stearate by mixing in a V blender for 2 min. Each batch was compressed as 400 mg tablets with 1.1 cm [7/16 in] (diameter) standard concave tooling (quarter set) using an Instrumented Stokes 512 tablet press. Hardness was measured with a Schleuniger 6D Hardness Tester. Tabletting results for Example 5 are summarized in Table 4. The co-processed composition with 50% and 75% mannitol could only be tabletted with the addition of lubricant. The co-processed composition with 25% mannitol was compressed with and without the addition of lubricant.

Figure 3:
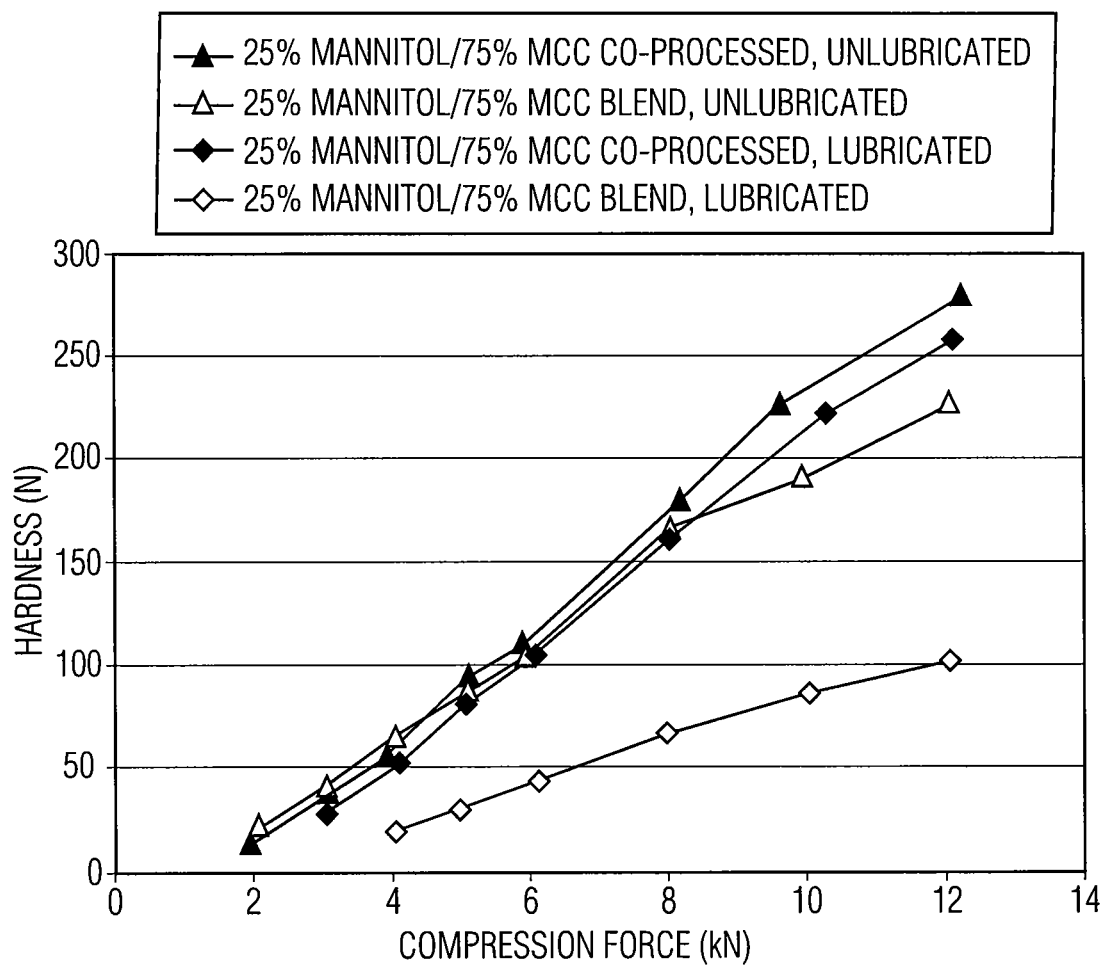
FIG. 3 shows the compaction profile of co-processed and blended 75% MCC/25% mannitol lubricated with 2% magnesium stearate.

Table 4A and FIG. 3 show the compaction profile of co-processed 75% MCC/250% mannitol and the compaction profile of blended 75% MCC/25% mannitol, with and without 2% magnesium stearate. As can be seen from FIG. 3, unlubricated co-processed 75% MCC/25% mannitol has slightly greater hardness than blended 75% MCC/250% mannitol, and lubricated co-processed MCC/mannitol showed consistently superior hardness than the corresponding lubricated blend.

TABLE 4A

Compaction Profile of 25% Mannitol/75% MCC

| Compaction Force (kN) | Weight (mg) | Thickness (mm) | Hardness (N) | Compaction Force (kN) | Weight (mg) | Thickness (mm) | Hardness (N) |
|---|---|---|---|---|---|---|---|
| Co-Processed 25% Mannitol/75% MCC, Unlubricated | | | | 25% Mannitol/75% MCC Blend, Unlubricated | | | |
| 1.95 | 413 | 6.52 | 14 | 2.08 | 386 | 6.17 | 22 |
| 3.08 | 416 | 6.01 | 38 | 3.04 | 390 | 5.68 | 41 |
| 3.94 | 413 | 5.68 | 56 | 4.06 | 392 | 5.31 | 65 |
| 5.90 | 405 | 5.15 | 111 | 5.94 | 393 | 4.91 | 105 |
| 8.17 | 408 | 4.79 | 181 | 8.03 | 393 | 4.64 | 150 |
| 9.63 | 411 | 4.69 | 226 | 9.94 | 395 | 4.45 | 191 |
| 12.22 | 406 | 4.48 | 279 | 12.05 | 395 | 4.32 | 227 |
| Co-processed 25% Mannitol/75% MCC, with 2% Mg Stearate | | | | 25% Mannitol/75% MCC blend, with 2% Mg Stearate | | | |
| 0.95 | 396 | 6.17 | 10 | 4.06 | 394 | 5.18 | 20 |
| 3.06 | 396 | 5.62 | 28 | 4.96 | 392 | 4.96 | 30 |
| 6.07 | 395 | 4.78 | 105 | 6.12 | 391 | 4.76 | 45 |
| 8.00 | 397 | 4.51 | 161 | 7.98 | 391 | 4.52 | 67 |
| 10.26 | 397 | 4.31 | 222 | 10.01 | 390 | 4.35 | 87 |
| 12.08 | 396 | 4.20 | 258 | 12.04 | 388 | 4.24 | 102 |

Figure 4:
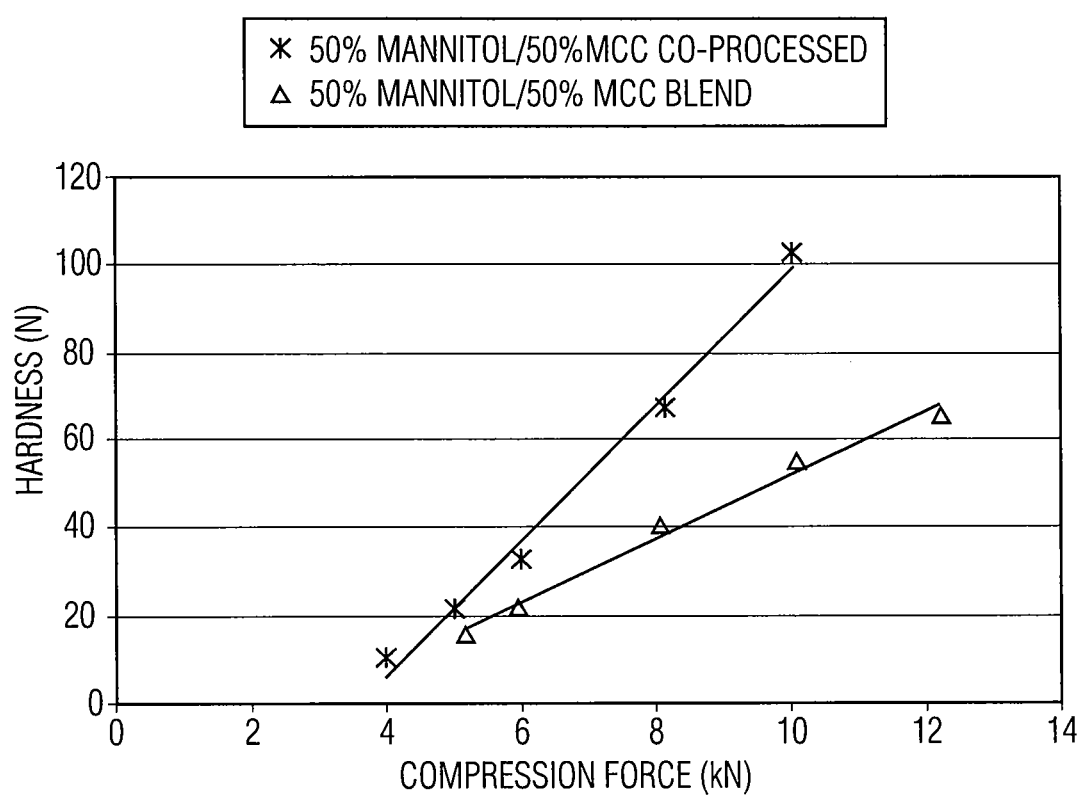
FIG. 4 shows the compaction profile of co-processed and blended 50% MCC/50% mannitol lubricated with 2% magnesium stearate.

Table 4B and FIG. 4 show the compaction profile of co-processed 50% MCC/50% mannitol and the compaction profile of blended 50% MCC/50% mannitol (PEARLITOL® 400 DC) with 2% magnesium stearate. As can be seen from FIG. 4, lubricated co-processed MCC/mannitol showed consistently superior hardness than the corresponding lubricated blend.

TABLE 4B

Compaction Profile 50% Mannitol/50% MCC

| Compaction Force (kN) | Weight (mg) | Thickness (mm) | Hardness (N) | Compaction Force (kN) | Weight (mg) | Thickness (mm) | Hardness (N) |
|---|---|---|---|---|---|---|---|
| Co-processed 50% Mannitol/50% MCC, with 2% Mg Stearate | | | | 50% Mannitol/50% MCC blend, with 2% Mg Stearate | | | |
| 3.98 | 405 | 5.44 | 10 | 5.14 | 406 | 4.97 | 16 |
| 4.99 | 403 | 5.20 | 21 | 5.94 | 404 | 4.82 | 22 |
| 5.98 | 401 | 5.02 | 33 | 8.06 | 405 | 4.59 | 41 |
| 8.13 | 407 | 4.70 | 67 | 10.06 | 403 | 4.45 | 55 |
| 10.03 | 408 | 4.51 | 103 | 12.22 | 402 | 4.36 | 66 |

Figure 5:
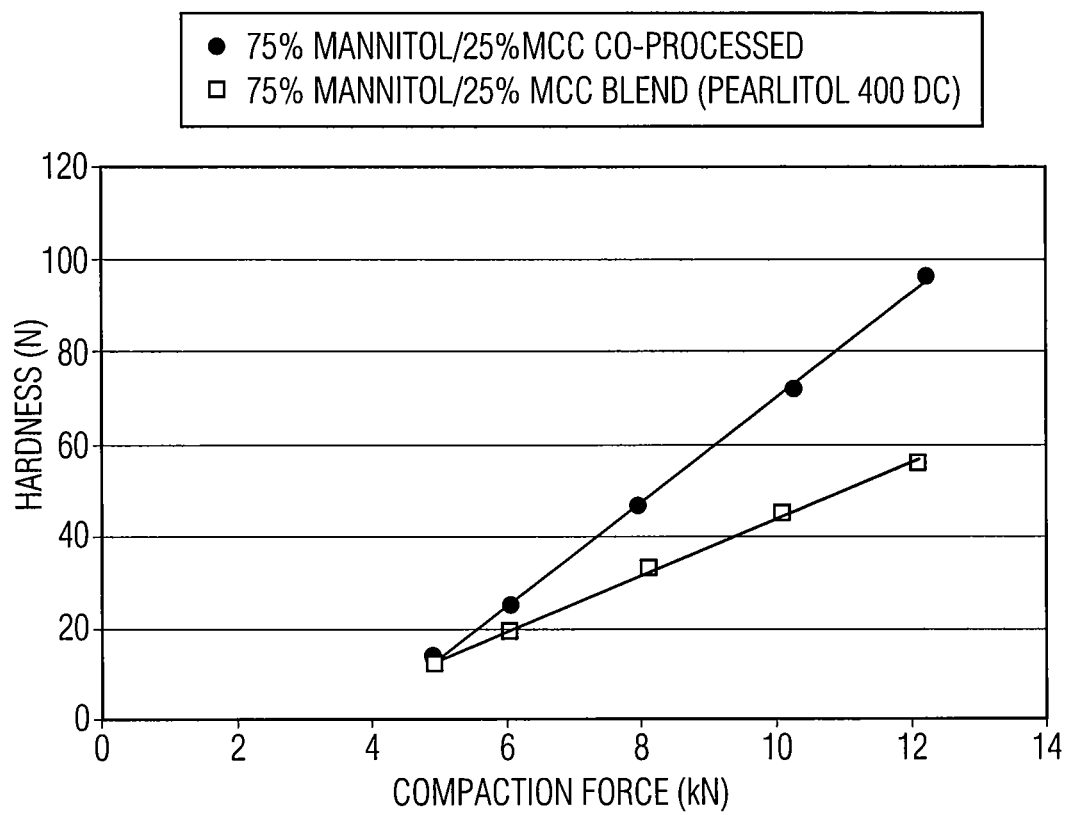
FIG. 5 shows the compaction profile of co-processed and blended 25% MCC/75% mannitol lubricated with 2% magnesium stearate.

Table 4C and FIG. 5 show the compaction profile of co-processed 25% MCC/75% mannitol and the compaction profile of blended 25% MCC/75% mannitol (PEARLITOL® 400 DC) with 2% magnesium stearate. As can be seen from FIG. 5, lubricated co-processed MCC/mannitol showed consistently superior hardness than the corresponding lubricated blend.

TABLE 4C

Compaction Properties of 75% Mannitol/25% MCC

| Co-processed 75% Mannitol/25% MCC, with 2% Mg Stearate | | | | 75% Mannitol/25% MCC blend, with 2% Mg Stearate | | | |
|---|---|---|---|---|---|---|---|
| Compaction Force (kN) | Weight (mg) | Thickness (mm) | Hardness (N) | Compaction Force (kN) | Weight (mg) | Thickness (mm) | Hardness (N) |
| 4.90 | 408 | 5.22 | 14 | 4.91 | 398 | 4.78 | 12 |
| 6.06 | 408 | 5.01 | 25 | 6.05 | 398 | 4.64 | 19 |
| 7.94 | 408 | 4.75 | 46 | 8.09 | 398 | 4.47 | 33 |
| 10.26 | 404 | 4.53 | 72 | 10.06 | 398 | 4.40 | 45 |
| 12.19 | 406 | 4.42 | 97 | 12.09 | 397 | 4.32 | 56 |

The compaction profiles of mannitol of three different particle sizes lubricated with magnesium stearate are given in Table 4D. The compaction profile of MCC lubricated with magnesium stearate is given in Table 4E.

TABLE 4D

Compaction Profile of Mannitol

| PEARLITOL ® 300 with 2% Mg Stearate | | | | PEARLITOL ® 400 with 2% Mg Stearate | | | |
|---|---|---|---|---|---|---|---|
| Compaction Force (kN) | Weight (mg) | Thickness (mm) | Hardness (N) | Compaction Force (kN) | Weight (mg) | Thickness (mm) | Hardness (N) |
| 3.02 | 400 | 4.80 | 12 | 3.02 | 403 | 4.84 | 10 |
| 4.04 | 401 | 4.68 | 18 | 4.10 | 403 | 4.72 | 15 |
| 6.12 | 404 | 4.51 | 31 | 6.00 | 403 | 4.58 | 26 |
| 8.06 | 400 | 4.42 | 42 | 8.09 | 404 | 4.48 | 39 |
| 9.95 | 400 | 4.37 | 53 | 10.16 | 403 | 4.42 | 48 |
| 11.83 | 399 | 4.33 | 64 | 11.94 | 405 | 4.38 | 55 |

| PEARLITOL ® 500 with 2% Mg Stearate | | | |
|---|---|---|---|
| Compaction Force (kN) | Weight (mg) | Thickness (mm) | Hardness (N) |
| 3.05 | 391 | 4.68 | 13 |
| 4.13 | 394 | 4.57 | 19 |
| 5.98 | 395 | 4.44 | 29 |
| 8.07 | 394 | 4.35 | 43 |
| 10.06 | 393 | 4.28 | 53 |
| 12.03 | 392 | 4.24 | 62 |

TABLE 4E

Compaction Profile of MCC AVICEL ® PH102 with 2% Mg Stearate

| Compaction Force (kN) | Weight (mg) | Thickness (mm) | Hardness (N) |
|---|---|---|---|
| 2.00 | 396 | 6.42 | 11 |
| 4.00 | 398 | 5.28 | 48 |
| 6.02 | 397 | 4.80 | 86 |
| 7.98 | 396 | 4.53 | 119 |
| 10.08 | 395 | 4.35 | 146 |
| 12.04 | 398 | 4.25 | 165 |

Table 5A shows the ratio of the compatibilities of co-processed mannitol/MCC and the corresponding blends. The compaction coefficient or compactability is the slope of tablet hardness-compaction force curve.

TABLE 5A

Compatibility of Mannitol/MCC

| Excipient | Co-Processed (N/kN) | Blend (N/kN) | Ratio of Co-Processes/Blend Compactabilities |
|---|---|---|---|
| 5% Mannitol/95% MCC, 2% lubricant[a] | 25.3 | 11.7 | 2.2 |
| 5% Mannitol/95% MCC, 1% lubricant | 26.6 | 15.1 | 1.8 |
| 20% Mannitol/80% MCC, 2% lubricant | 27.5 | 12.0 | 2.3 |

TABLE 5A-continued

Compatibility of Mannitol/MCC

| Excipient | Co-Processed (N/kN) | Blend (N/kN) | Ratio of Co-Processes/Blend Compactabilities |
|---|---|---|---|
| 20% Mannitol/80% MCC, 1% lubricant | 35.2 | 14.6 | 2.4 |
| 25% Mannitol/75% MCC, unlubricated | 27.0 | 21.2 | 1.3 |
| 25% Mannitol/75% MCC, 2% lubricant | 26.2 | 10.5 | 2.5 |
| 50% Mannitol/50% MCC, 2% lubricant | 15.4 | 7.2 | 2.1 |
| 75% Mannitol/25% MCC, 2% lubricant[a] | 11.3 | 6.1 | 1.9 |

[a]Lubricant was magnesium stearate.

The compactability of lubricated co-processed mannitol/MCC was significantly greater than that of corresponding lubricated blends of mannitol/MCC for weight ratios of 25%/75%; 50%/50% and 75%/25% mannitol/MCC. The co-processed MCC/mannitol thus appears to have a better lubricant resistance than the blended MCC/mannitol. The same almost two fold difference in compactability between the co-processed and blended MCC/mannitol is seen with 1% magnesium stearate and with 2% magnesium stearate.

At 25% mannitol, the compactability of co-processed MCC/mannitol is not significantly affected by the addition of 2% lubricant, whereas the compactability of the corresponding blends was significantly reduced by the addition of 2% lubricant. This is shown in Table 5B.

TABLE 5B

Lubricant Sensitivity of 25% Mannitol/75% MCC

| | Unlubricated (N/kN) | Lubricated (N/kN) | Lubricant Sensitivity |
|---|---|---|---|
| Co-processed | 27.0 | 26.2 | 1.03 |
| Blend | 21.2 | 10.5 | 2.02 |

For the 25% mannitol/75% MCC co-processed materials, lubricated with 2% magnesium stearate, the ratio of the unlubricated compactability to the lubricated compactability (lubricant sensitivity) was 1.03. For the 25% mannitol/75% MCC blends, the lubricant sensitivity was 2.02.

The compaction coefficients of the reference materials (100% mannitol and 100% MCC) are summarized in Table 6. The effect of particle size on compactability of PEARLITOL® DC is not significant.

TABLE 6

Compaction Coefficient of Reference Materials

| Reference Material | Compaction coefficient (N/kN) |
|---|---|
| PEARLITOL ® 300 DC, Lubricated | 5.9 |
| PEARLITOL ® 400 DC, Lubricated | 5.2 |
| PEARLITOL ® 500 DC, Lubricated | 5.6 |
| AVICEL ® PH 102, Lubricated | 15.7 |

Example 6

This example shows that co-processed MCC/mannitol exhibits significantly better lubricant resistance than the blended MCC/mannitol as well as AVICEL® PH and that co-processed MCC/mannitol exhibits at least 100% higher compactability than the corresponding blends when tested under lubrication.

Co-processed and blended MCC/mannitol were compared (both lubricated and unlubricated) to assess the effect of lower mannitol content. Samples were prepared as described in Example 5. The following materials were used: 0% mannitol/100% MCC; 5% mannitol/95% MCC; 10% mannitol/90% MCC; 15% mannitol/85% MCC; 20% mannitol/80% MCC; and PEARLITOL® 100 SD (100% mannitol). The compaction coefficients of the blended and co-processed compositions are summarized in Table 7A and Table 7B, below.

Example 7

This example shows that the protective action of co-processed mannitol on MCC lubricant sensitivity fell off with decreasing mannitol content when mannitol is below 5%.

Co-processed and blended MCC/mannitol were compared (both lubricated and unlubricated) to assess the effect of very low mannitol content (less than 5%), using the blending, lubrication and tabletting methods of Example 5. The following materials were used: 0.5% mannitol/99.5% MCC; 1% mannitol/99% MCC; and 2.5% mannitol/97.5% MCC. The compaction coefficient of co-processed and blended mannitol/MCC obtained in Examples 5-7 are summarized in Table 7A and 7B. For 0% mannitol (100% MCC) and 100% mannitol (0% MCC), the "co-processed" and "blended" values are the same because each of these compositions does not contain the other ingredient.

TABLE 7A

Compaction Coefficient of Mannitol/MCC

| Excipients, lubricated with 0.5% magnesium stearate | Co-Processed (N/kN) | Blend (N/kN) | Ratio of Co-Processed/Blend Compactabilities |
|---|---|---|---|
| 0% MANNITOL/100% MCC* | 22.6 | 22.6 | 1.00 |
| 5% Mannitol/95% MCC | 28.9 | 21.0 | 1.38 |
| 10% Mannitol/90% MCC | 34.7 | 18.5 | 1.87 |
| 15% Mannitol/85% MCC | 29.0 | 18.7 | 1.55 |
| 20% Mannitol/80% MCC | 30.2 | 17.3 | 1.75 |
| 25% Mannitol/75% MCC | 26.6 | 16.7 | 1.59 |
| 50% Mannitol/50% MCC | 18.6 | 11.8 | 1.58 |
| 75% Mannitol/25% MCC | 12.5 | 9.84 | 1.27 |
| 100% Mannitol | 10.6 | 10.6 | 1.00 |

TABLE 7B

Compaction Coefficient of Mannitol/MCC

| Excipients, lubricated with 2% magnesium stearate | Co-Processed (N/kN) | Blend (N/kN) | Ratio of Co-Processed/Blend Compactabilities |
|---|---|---|---|
| AVICEL ® PH 102 | 15.7 | 15.7 | 1.00 |
| 0% MANNITOL/100% MCC* | 12.1 | 12.1 | 1.00 |
| 0.5% Mannitol/99.5% MCC | 16.0 | 12.2 | 1.31 |
| 1.0% Mannitol/99.0% MCC | 17.8 | 12.2 | 1.46 |
| 2.5% Mannitol/97.5% MCC | 21.1 | 13.1 | 1.61 |
| 5% Mannitol/95% MCC | 25.3 | 11.7 | 2.15 |
| 10% Mannitol/90% MCC | 26.3 | 11.7 | 2.24 |
| 15% Mannitol/85% MCC | 27.5 | 12.4 | 2.22 |
| 20% Mannitol/80% MCC | 27.5 | 12.0 | 2.29 |
| 25% Mannitol/75% MCC | 24.2 | 11.0 | 2.19 |
| 50% Mannitol/50% MCC | 15.4 | 7.2 | 2.14 |
| 75% Mannitol/25% MCC | 11.3 | 6.1 | 1.85 |
| 100% Mannitol | 5.2 | 5.2 | 1.00 |

Figure 6:
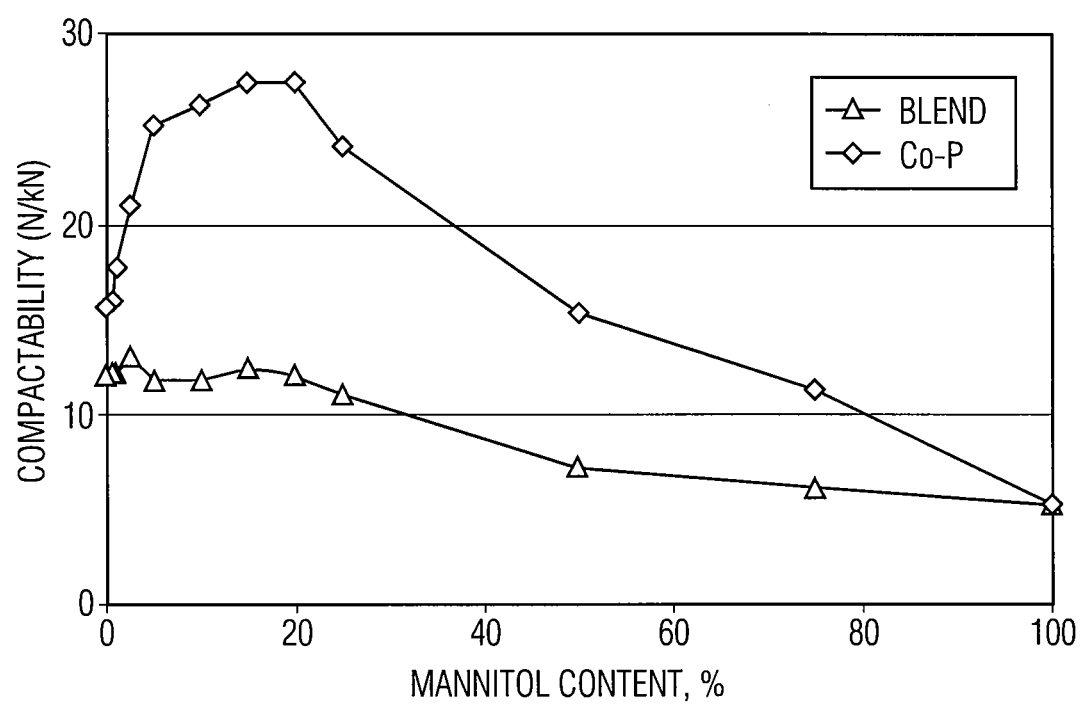
FIG. 6 show the compaction coefficient (compactability) of co-processed and blended MCC/mannitol lubricated with 2% magnesium stearate as a function of mannitol content.

FIG. 6 show the compaction coefficient (compactability) of co-processed and blended MCC/mannitol lubricated with 2% magnesium stearate as a function of mannitol content. As can be seen from Table 7A, Table 7B, and FIG. 6, the compactability of lubricated MCC/mannitol blends was not significantly affected by mannitol content. 0% MANNITOL/100% MCC is less compactable than AVICEL® PH 102 when tested under lubrication. The compactability of co-processed MCC/mannitol was significantly greater than that of the corresponding blends as well as the lubricated MCC samples. The compactability of co-processed MCC/mannitol was not affected by mannitol content within the range of 5% to 25% (w/w) mannitol.

Lubricant sensitivity as a function of mannitol content for co-processed and blended mannitol/MCC is shown in Table 8. Unlubricated blends of 50% mannitol/50% MCC and 75% mannitol/25% MCC could not be tabletted so it was not possible to determine lubricant sensitivity for these materials.

TABLE 8

Lubricant Sensitivity of Mannitol/MCC as a Function of Mannitol Concentration

| % Mannitol | Blend | Co-processed |
|---|---|---|
| 0%[a] | 2.19 | 2.19 |
| 5%[b] | ND[c] | 1.43 |
| 10%[a] | 2.11 | 1.73 |
| 25%[b] | 2.02 | 1.03 |

[a]About 90 micron particle size
[b]About 50 micron particle size
[c]ND = not determined As can be seen from Table 8, mannitol is much more effective in reducing the lubricant sensitivity of microcrystalline cellulose when it is present in co-processed mixture.

Example 8

Further tests were conducted to evaluate the effect of lubricant content on the lubricant sparing properties of co-processed MCC/mannitol. The compactability of 0% mannitol/100% MCC; 5% mannitol/95% MCC (about 50 microns particle size); 10% mannitol/90% MCC (about 90 microns particle size); 25% mannitol/75% MCC (about 50 microns particle size); PROSOLV® 90; and AVICEL® PH-102 was determined by varying the amount of lubricant used, using the blending, lubrication, and tabletting methods of Example 5. The results are shown in Table 9.

TABLE 9

Effect of Lubricant Content on Compactability

| % Mg Stearate | AVICEL® PH-102/ Pearlitol SD 200 Blends | | | PROSOLV® 90 | AVICEL® PH-102 |
|---|---|---|---|---|---|---|
| | 5%[a] | 10%[b] | | 25%[a] | | |
| 0% | 36.1 | 37.1 | 25.5 | 27 | 35.1 | 35.2 |
| 0.5% | ND[c] | 22.6 | 18.0 | ND[c] | ND[c] | ND[c] |
| 1% | 26.6 | 25.1 | 15.1 | 29.7 | 25.3 | 24.2 |
| 2% | 25.3 | 21.5 | 12.1 | 24.2 | 21 | 16.1 |
| 3% | 17.5 | ND[c] | ND[c] | 21.7 | 15.8 | 12.9 |

[a]About 50 microns particle size
[b]About 90 microns particle size
[c]Not determined The lubricant sensitivity of PROSOLV® 90 at 2% magnesium stearate is 1.67.

Example 9

Ejection force was determined by tableting in an instrumented tablet press. The ejection force data for samples with various mannitol content was compared at a compaction force of 10 kN and summarized in Table 10.

TABLE 10

Ejection Force at 10 kN Compaction Force

| Mannitol (%) | Ejection Force (N) |
|---|---|
| 0 | 147 |
| 5 | 137 |
| 10 | 132 |
| 15 | 114 |
| 20 | 111 |
| 25 | 113 |
| 50 | 139 |
| 75 | 172 |
| 100 | 246 |

When the mannitol content is between 15%-25%, the ejection force of the co-processed MCC/mannitol was lower than that of PROSOLV® and AVICEL® PH 102 when tested under lubrication. Low ejection force is desirable for tabletting.

Example 10

Comparative tests were conducted for compactability of tablets made from regular lactose with 30% co-processed MCC/mannitol (mannitol/MCC 5%/95% and 20%/80%) against AVICEL® PH 102 and PROSOLV® 90, using the blending, lubrication and tabletting methods of Example 5. This shows the dilution potential of the inventive compositions. Tabletting results for Example 10 are summarized in Table 11.

TABLE 11

Compaction Profile Co-processed MCC/mannitol, AVICEL ® PH-102 and PROSOLV ® 90

| Compaction Force (kN) | Weight (mg) | Thickness (mm) | Hardness (N) | Compaction Force (kN) | Weight (mg) | Thickness (mm) | Hardness (N) |
|---|---|---|---|---|---|---|---|
| Co-processed 5% mannitol/95% MCC, with 2% Mg Stearate | | | | Co-processed 20% mannitol/80% MCC, with 2% Mg Stearate | | | |
| 4 | 398 | 4.83 | 12 | 3.91 | 398 | 4.78 | 15 |
| 5 | 398 | 4.65 | 20 | 5.02 | 398 | 4.61 | 23 |
| 6 | 397 | 4.57 | 26 | 6.07 | 397 | 4.49 | 32 |
| 8 | 398 | 4.4 | 44 | 7.92 | 396 | 4.33 | 49 |
| 10 | 398 | 4.28 | 59 | 9.99 | 396 | 4.26 | 66 |
| 12 | 397 | 4.21 | 74 | 12.11 | 397 | 4.2 | 84 |
| AVICEL ® PH-102 with 2% Mg Stearate | | | | PROSOLV ® 90 with 2% Mg Stearate | | | |
| 4.06 | 401 | 4.81 | 10 | 4 | 408 | 4.92 | 10 |
| 5.1 | 397 | 4.65 | 16 | 5 | 409 | 4.75 | 17 |
| 6.15 | 398 | 4.54 | 22 | 6 | 409 | 4.64 | 25 |
| 8 | 399 | 4.4 | 36 | 8 | 410 | 4.48 | 38 |
| 10.06 | 400 | 4.31 | 52 | 10 | 410 | 4.38 | 51 |
| 11.96 | 401 | 4.24 | 65 | 12 | 410 | 4.3 | 67 |

The compactability of formulations made with co-processed MCC/mannitol is better than that of formulations made with AVICEL® PH 102 and PROSOLV® 90. At 30% use level in regular lactose with 2% magnesium stearate, co-processed MCC/mannitol was significantly more compactable than AVICEL® PH 102 and PROSOLV® 90. The 20% mannitol co-processed composition was more compactable than the 5% mannitol product at 30% use level in regular lactose with 2% magnesium stearate.

Example 11

To evaluate the influence of compression speed on the compactability of AVICEL® PH-102 and co-processed MCC:mannitol 90:10, these materials were compressed on a compaction simulator at speed of 100, 150, 200, 250, 300 mm/s, under the lubrication of 1% magnesium stearate. The compression speeds correspond to the vertical speed of the upper punch compressing the powder. A speed of 100 mm/s is similar to the tabletting speed (or dwell time) of a development press equipped with B-type tooling. The highest speed, i.e. 300 mm/s, is equivalent to today's high speed production presses.

TABLE 12

High Speed Tableting Properties

| | Compact slope ($10^{-2}$) | |
|---|---|---|
| Speed (mm/s) | Co-processed 90% MCC/10% mannitol | AVICEL ® PH-102 |
| 100 | 6.1 | 4.8 |
| 150 | 5.8 | 4.7 |
| 200 | 5.5 | 4.7 |
| 250 | 5.0 | 4.3 |
| 300 | 5.1 | 4.6 |

As can be seen from Table 12, co-processed MCC/mannitol is more compactable than AVICEL® PH-102 microcrystalline cellulose regardless of compaction speed, despite the reduction of compactability at higher speed.

Example 12

Comparative tests were conducted for compactability of tablets made from granular acetaminophen with co-processed MCC/mannitol (mannitol/MCC 10%/90%) with particle size of 50 microns and 90 microns, AVICEL® PH 101, AVICEL® PH 102 and AVICEL® PH 105 using the blending, lubrication and tabletting methods of Example 5.

Tablet formulation contained 50 wt % granular acetaminophen, and 0.5 wt % magnesium stearate. Tables 13 and 14 shows the compaction profile of the tablets made from granular acetaminophen and binder/fillers lubricated with 0.5% magnesium stearate.

TABLE 13

Compaction Profile of Binders with Smaller Particle Size

| AVICEL ® PH-105 formulation with 0.5% Mg Stearate | | | | AVICEL ® PH-101 formulation with 0.5% Mg Stearate | | | |
|---|---|---|---|---|---|---|---|
| Compaction Force (kN) | Weight (mg) | Thickness (mm) | Hardness (N) | Compaction Force (kN) | Weight (mg) | Thickness (mm) | Hardness (N) |
| 3.14 | 385 | 4.68 | 16 | 2.00 | 402 | 5.50 | 4 |
| 4.02 | 380 | 4.61 | 21 | 3.23 | 408 | 5.12 | 11 |

TABLE 13-continued

Compaction Profile of Binders with Smaller Particle Size

| 5.03 | 393 | 4.46 | 32 | 4.09 | 407 | 4.98 | 15 |
|---|---|---|---|---|---|---|---|
| 5.98 | 397 | 4.34 | 48 | 5.10 | 408 | 4.79 | 22 |
| 8.04 | 393 | 4.26 | 54 | 6.17 | 411 | 4.70 | 26 |
| 9.98 | 400 | 4.17 | 70 | 7.94 | 411 | 4.55 | 34 |
| 12.01 | 396 | 4.05 | 88 | 10.08 | 413 | 4.44 | 43 |
| | | | | 12.01 | 411 | 4.31 | 46 |

Co-processed 10% mannitol/90% MCC (50 microns) formulation with 0.5% Mg Stearate

| Compaction Force (kN) | Weight (mg) | Thickness (mm) | Hardness (N) |
|---|---|---|---|
| 3.09 | 405 | 5.05 | 9 |
| 3.99 | 405 | 4.81 | 14 |
| 5.04 | 408 | 4.66 | 20 |
| 6.10 | 407 | 4.54 | 27 |
| 7.98 | 404 | 4.37 | 37 |
| 9.93 | 405 | 4.27 | 49 |
| 12.04 | 404 | 4.13 | 61 |

As can be seen from Table 13, the compactability of formulations made with 50 micron co-processed MCC/mannitol is 36% better than that of formulations made with AVICEL® PH-101. The formulation of AVICEL® PH-105 has the best compactability since AVICEL® PH-105 has the smallest particle size and largest surface area among all binders tested.

TABLE 14

Compaction Profile of APAP Formulations (binders particle size 90 microns)

| Co-processed 10% mannitol/90% MCC (90 microns) formulation with 0.5% Mg Stearate | | | | AVICEL ® PH-102 formulation with 0.5% Mg Stearate | | | |
|---|---|---|---|---|---|---|---|
| Compaction Force (kN) | Weight (mg) | Thickness (mm) | Hardness (N) | Compaction Force (kN) | Weight (mg) | Thickness (mm) | Hardness (N) |
| 3.03 | 399 | 5.11 | 4 | 4.06 | 403 | 4.97 | 6 |
| 4.05 | 400 | 4.95 | 8 | 5.00 | 403 | 4.77 | 9 |
| 4.99 | 399 | 4.81 | 14 | 6.06 | 406 | 4.67 | 13 |
| 5.98 | 398 | 4.64 | 21 | 8.10 | 405 | 4.48 | 20 |
| 8.15 | 400 | 4.43 | 32 | 9.90 | 406 | 4.40 | 27 |
| 10.04 | 401 | 4.32 | 41 | 11.95 | 405 | 4.31 | 31 |
| 12.05 | 400 | 4.24 | 49 | | | | |

As can be seen from Table 14, the compactability of formulations made with 90 micron co-processed MCC/mannitol is 55% better than that of formulations made with AVICEL® PH-102. For both AVICEL® PH-102 and coprocessed MCC/mannitol, small particle size particulate enhances the compactability of the APAP formulation.

Five minute friability of tablets of binders in 50% granular APAP (acetaminophen) lubricated with 0.5% Mg Stearate, 40 rpm are summarized in Table 15.

TABLE 15

Five Minute Friability of APAP Tablets

| | Co-processed 10% mannitol/90% MCC Formulation | AVICEL ® PH-102 Formulation |
|---|---|---|
| Friability | 0.33% | 0.46% |

As can be seen from Table 15, the friability of tablets of 90 microns co-processed 10% mannitol/90% MCC is less than that of AVICEL® PH-102 tablets.

Example 13

Tablet disintegration time was tested in disintegration bath evaluated at 37° C. in deionized water. Table 16 shows the disintegration data of the tablets made from AVICEL® PH-102 and from co-processed 10% mannitol/90% MCC with 90 micron particle size, each of which was lubricated with 0.5% magnesium stearate.

TABLE 16

Disintegration Time of Tablets Containing 0.5% Magnesium Stearate

| | AVICEL ® PH-102 | | Co-processed 10% mannitol/90% MCC | |
|---|---|---|---|---|
| Compaction Force (kN) | Hardness (N) | Disintegration (min) | Hardness (N) | Disintegration (min) |
| 2.00 | 29 | 0.2 | 30 | 0.22 |
| 4.00 | 85 | 0.5 | 105 | 0.48 |
| 6.00 | 139 | 2.1 | 174 | 3.05 |
| 12.00 | 255 | 16.7 | 327 | 11.68 |

Table 17 shows the disintegration data of the dicalcium phosphate (DCP) tablet made from AVICEL® PH-102 and co-processed 10% mannitol/90% MCC with 90 micron particle size, lubricated with 2% magnesium stearate.

TABLE 17

Disintegration Time of DCP Tablets Containing 2% Magnesium Stearate

| Compaction Force (kN) | 57.5% DCP/42.5% AVICEL ® PH-102 | | 57.5% DCP/42.5% Co-processed 10% mannitol/90% MCC | |
|---|---|---|---|---|
| | Hardness (N) | Disintegration (min) | Hardness (N) | Disintegration (min) |
| 2 | 0 | 0.25 | 0 | 0.24 |
| 4 | 15 | 0.54 | 23 | 0.50 |
| 6 | 33 | 1.30 | 36 | 1.38 |
| 12 | 88 | 21.63 | 98 | 11.82 |

As can be seen from Tables 16 and 17, tablets of co-processed 10% mannitol/90% MCC disintegrated faster than those of AVICEL® PH-102.

Coprocessed MCC/mannitol exhibits significant lubricant sparing effect and gives harder, less friable and faster disintegrating tablets than MCC. MCC/mannitol also gives thinner tablets, relative to MCC.

Having described the invention, we now claim the following and their equivalents.

What is claimed is:

1. A co-processed composition consisting essentially of a spray dried particulate of co-processed microcrystalline cellulose and at least one sugar alcohol containing four to six carbon atoms, in which:
   the ratio of microcrystalline cellulose to the at least one sugar alcohol is 70:30 to 95:5,
   said composition has a loose bulk density of 0.20 g/cm³ to 0.55 g/cm³, and
   the ratio of the compactability of an unlubricated composition to the compactability of a lubricated composition is 1.6 or less when the lubricated composition additionally comprises about 1% magnesium stearate;
   wherein said composition is an excipient composition.

2. The composition of claim 1 in which the at least one sugar alcohol has five to six carbon atoms.

3. The composition of claim 2 in which the mean particle size of the particulate is about 50 microns to about 200 microns.

4. The composition of claim 3 in which the at least one sugar alcohol is mannitol and the ratio of microcrystalline cellulose to mannitol is about 75:25 to about 90:10.

5. The composition of claim 1 in which the mean particle size of the particulate is about 50 microns to about 200 microns; and the at least one sugar alcohol is mannitol.

6. The composition of claim 5 in which the ratio of microcrystalline cellulose to mannitol is about 75:25 to about 90:10.

7. A compressible tablet formulation comprising at least one active, at least one pharmaceutically acceptable excipient, and the co-processed composition of 6.

8. A compressible tablet formulation comprising at least one active, at least one pharmaceutically acceptable excipient, and the co-processed composition of 1.

9. The compressible tablet formulation of claim 8 additionally comprising about 0.5 wt % to about 3.0 wt % of a lubricant.

10. The composition of claim 1 consisting of said microcrystalline cellulose and said at least one sugar alcohol.

11. A method for preparing the co-processed composition of claim 1, the method comprising the steps of:
   (a) forming an aqueous slurry of said microcrystalline cellulose and said sugar alcohol, the slurry having a solids content and temperature to ensure dissolution of the at least one sugar alcohol, and
   (b) spray drying the slurry.

12. The method of claim 11 in which the slurry additionally comprises ammonium hydroxide.

13. The method of claim 11 in which the sugar alcohol is mannitol.

* * * * *